(12) United States Patent
Feng et al.

(10) Patent No.: US 8,067,155 B2
(45) Date of Patent: Nov. 29, 2011

(54) RECEPTOR TYROSINE KINASE ASSAYS

(75) Inventors: Wei Feng, Fremont, CA (US); William Raab, San Francisco, CA (US); Philip Achacoso, Union City, CA (US); Thomas Wehrman, East Palo Alto, CA (US); Keith R. Olson, Pleasanton, CA (US)

(73) Assignee: DiscoveRx Corporation, Fremont, CA (US)

( * ) Notice: Subject to any disclaimer, the term of this patent is extended or adjusted under 35 U.S.C. 154(b) by 0 days.

(21) Appl. No.: 12/536,667

(22) Filed: Aug. 6, 2009

(65) Prior Publication Data

US 2010/0041052 A1    Feb. 18, 2010

Related U.S. Application Data

(60) Provisional application No. 61/089,799, filed on Aug. 18, 2008.

(51) Int. Cl.
*C12Q 1/00*      (2006.01)
*G01N 33/53*     (2006.01)

(52) U.S. Cl. .................. 435/4; 435/7.8; 435/7.9
(58) Field of Classification Search .................. None
See application file for complete search history.

(56) References Cited

U.S. PATENT DOCUMENTS

| | | | |
|---|---|---|---|
| 4,708,929 A * | 11/1987 | Henderson ..................... 435/7.5 |
| 5,188,938 A * | 2/1993 | Khanna et al. ................ 435/7.7 |
| 5,604,091 A | 2/1997 | Henderson |
| 5,667,980 A | 9/1997 | Pawson et al. |
| 5,773,237 A | 6/1998 | Wong et al. |
| 5,786,454 A * | 7/1998 | Waksman et al. ............. 530/402 |
| 5,891,650 A * | 4/1999 | Godowski et al. ........... 435/7.21 |
| 5,914,237 A | 6/1999 | Godowski et al. |
| 5,976,893 A | 11/1999 | Dennis et al. |
| 6,025,145 A | 2/2000 | Godowski et al. |
| 6,280,964 B1 * | 8/2001 | Kavanaugh et al. ........... 435/7.8 |
| 6,287,784 B1 | 9/2001 | Godowski et al. |
| 6,342,345 B1 | 1/2002 | Blau et al. |
| 6,413,730 B1 | 7/2002 | Holland et al. |
| 7,135,325 B2 | 11/2006 | Naqvi |
| 2002/0106739 A1 | 8/2002 | Oakley et al. |
| 2004/0038298 A1 | 2/2004 | Michnick et al. |
| 2004/0161787 A1 | 8/2004 | Michnick et al. |
| 2005/0287522 A1 | 12/2005 | Blau et al. |

(Continued)

FOREIGN PATENT DOCUMENTS

WO    WO 8602666 A *    5/1986

(Continued)

OTHER PUBLICATIONS

Blakely et al., (Nature Biotechnology. Feb. 2000.18:218-222).*

(Continued)

*Primary Examiner* — Cherie M Woodward
(74) *Attorney, Agent, or Firm* — David J. Aston; Peters Vermy, LLP

(57) ABSTRACT

Methods for detecting phosphorylation of receptor tyrosine kinases ("RTKs") upon activation are provided. The method employs cells comprising two fusion products: (1) an RTK fused to a small fragment of β-galactosidase and (2) a phosphotyrosine binding peptide fused to the large fragment of β-galactosidase, where the 2 fragments weakly complex to form an active enzyme, and optionally a construct for a cytosolic RTK phosphorylating kinase, when the RTK does not autophosphoryate. To detect phosphorylation a β-galactosidase substrate is added to the cells, whereby product formation indicates the occurrence of phosphorylation.

9 Claims, 9 Drawing Sheets

U.S. PATENT DOCUMENTS

| | | |
|---|---|---|
| 2006/0199226 A1 | 9/2006 | Schiffer |
| 2007/0015232 A1 | 1/2007 | Olson et al. |
| 2007/0105160 A1 | 5/2007 | Fung et al. |
| 2007/0275397 A1* | 11/2007 | Wehrman et al. ............ 435/6 |
| 2008/0010310 A1 | 1/2008 | Sprowls |
| 2009/0098588 A1 | 4/2009 | Wehrman et al. |
| 2010/0041052 A1 | 2/2010 | Feng et al. |

FOREIGN PATENT DOCUMENTS

| | | |
|---|---|---|
| WO | 0229410 A2 | 4/2002 |
| WO | 2005113838 A2 | 12/2005 |
| WO | 2010042921 A1 | 4/2010 |

OTHER PUBLICATIONS

Vidal et al., "Gene trap analysis of germ cell signaling to Sertoli cells: NGF-TrkA mediated induction of Fra1 and Fos by post-meiotic germ cells." (J Cell Sci. Jan. 2001. 114(2):435-443).*

Bruce T. Blakely, et al., "Epidermal growth factor receptor dimerization monitored in live cells," Nature Biotechnology, Feb. 2000, vol. 18, 218-222.

Tom S. Wehrman, et al., "Enzymatic detection of protein translocation," Nature Methods, Jul. 2005, vol. 2, 521-527.

Richard M. Eglen, "Enzyme fragment complementation: A flexible high throughput screening assay technology," Assay and Drug Development Technologies, 2002, vol. 1, 97-104.

Tom S. Wehrman, et al., "A system for quantifying dynamic protein interactions defines a role for Herceptin in modulating ErbB interactions," PNAS, Dec. 2006, vol. 103, 19063-19068.

Mark M. Hammer, et al., "A novel enzyme complementation-based assay for monitoring G-protein-coupled receptor internalization," FASEB J, 2007, vol. 21, 3827-3834.

Fabio Rossi, et al., "Monitoring protein-protein interactions in intact eukaryotic cells by β-galactosidase complementation," PNAS, 1997, vol. 94, 8405-8410.

Xiaoning Zhao, et al., "A homogeneous enzyme fragment complementation-based β-arrestin translocation assay for high-throuput screening of G-protein-coupled receptors," J Mol Screening, 2008, vol. 13, 737-747.

Richard M. Eglen, et al., "β-galactosidase enzyme fragment complementation as a novel technology for high throughput screening," Combinatorial Chemistry & High Throughput Screening, 2003, vol. 6, 381-387.

William A. Mohler, et al., "Gene expression and cell fusion analyzed by lacZ complementation in mammalian cells," PNAS, 1996, vol. 93, 12423-12427.

Tom Wehrman, et al., "Structural and mechanistic insights into nerve growth factor interactions with the TrkA and p75 receptors," Neuron, 2007, vol. 53, 25-38.

Graham Carpenter, "Receptor tyrosine kinase substrates: src homology domains and signal transduction," FASEB J. 6:3283-3289 (1992).

Debbie L. Graham, et al., "Application of β-Galactosidase Enzyme Complementation Technology as a High Throughput Screening Format for Antagonists of the Epidermal Growth Factor Receptor," J. Biomol. Screen., Dec. 2001; 6(6):401-411.

Frank H. Büttner, et al., "Evaluation of the InteraX™ System Technology in a High-Throuput Screening Environment," J. Biomol. Screen., Aug. 2005; 10(5):485-494.

Philip K. Tan, et al., "Monitoring Interactions between Receptor Tyrosine Kinases and Their Downstream Effector Proteins in Living Cells Using Bioluminescence Resonance Energy Transfer," Mod. Pharmacol., Dec. 2007; 72:1440-1446.

* cited by examiner

SEQUENCE LISTING

<160> NUMBER OF SEQ ID NOS: 2

<210> SEQ ID NO 1
<211> LENGTH: 1589
<212> TYPE: PRT
<213> ORGANISM: Artificial
<220> FEATURE:
<223> OTHER INFORMATION: Enzyme fragment

<400> SEQUENCE: 1

Met Asp Leu Leu Pro Pro Lys Pro Lys Tyr Asn Pro Leu Arg Asn Glu
1               5                   10                  15

Ser Leu Ser Ser Leu Glu Glu Gly Ala Ser Gly Ser Thr Pro Pro Glu
            20                  25                  30

Glu Leu Pro Ser Pro Ser Ala Ser Ser Leu Gly Pro Ile Leu Pro Pro
        35                  40                  45

Leu Pro Gly Asp Asp Ser Pro Thr Thr Leu Cys Ser Phe Phe Pro Arg
    50                  55                  60

Met Ser Asn Leu Arg Leu Ala Asn Pro Ala Gly Gly Arg Pro Gly Ser
65                  70                  75                  80

Lys Gly Glu Pro Gly Arg Ala Ala Asp Asp Gly Glu Gly Ile Val Gly
                85                  90                  95

Ala Ala Met Pro Asp Ser Gly Pro Leu Pro Leu Leu Gln Asp Met Asn
            100                 105                 110

Lys Leu Ser Gly Gly Gly Gly Arg Arg Thr Arg Val Glu Gly Gly Gln
        115                 120                 125

Leu Gly Gly Glu Glu Trp Thr Arg His Gly Ser Phe Val Asn Lys Pro
    130                 135                 140

Thr Arg Gly Trp Leu His Pro Asn Asp Lys Val Met Gly Pro Gly Val
145                 150                 155                 160

Ser Tyr Leu Val Arg Tyr Met Gly Cys Val Glu Val Leu Gln Ser Met
                165                 170                 175

Arg Ala Leu Asp Phe Asn Thr Arg Thr Gln Val Thr Arg Glu Ala Ile
            180                 185                 190

Ser Leu Val Cys Glu Ala Val Pro Gly Ala Lys Gly Ala Thr Arg Arg
        195                 200                 205

Arg Lys Pro Cys Ser Arg Pro Leu Ser Ser Ile Leu Gly Arg Ser Asn
    210                 215                 220

Leu Lys Phe Ala Gly Met Pro Ile Thr Leu Thr Val Ser Thr Ser Ser
225                 230                 235                 240

Leu Asn Leu Met Ala Ala Asp Cys Lys Gln Ile Ile Ala Asn His His
                245                 250                 255

Met Gln Ser Ile Ser Phe Ala Ser Gly Gly Asp Pro Asp Thr Ala Glu
            260                 265                 270

Tyr Val Ala Tyr Val Ala Lys Asp Pro Val Asn Gln Arg Ala Cys His
        275                 280                 285

Ile Leu Glu Cys Pro Glu Gly Leu Ala Gln Asp Val Ile Ser Thr Ile
    290                 295                 300

Gly Gln Ala Phe Glu Leu Arg Phe Lys Gln Tyr Leu Arg Asn Pro Pro
305                 310                 315                 320

Lys Leu Val Thr Pro His Asp Arg Met Ala Gly Phe Asp Gly Ser Ala
                325                 330                 335

Trp Asp Glu Glu Glu Glu Glu Pro Pro Asp His Gln Tyr Tyr Asn Asp
            340                 345                 350

-continued

```
Phe Pro Gly Lys Glu Pro Pro Leu Gly Gly Val Val Asp Met Arg Leu
            355                 360                 365

Arg Glu Gly Ala Ala Pro Gly Ala Ala Arg Pro Thr Ala Pro Asn Ala
        370                 375                 380

Gln Thr Pro Ser His Leu Gly Ala Thr Leu Pro Val Gly Gln Pro Val
385                 390                 395                 400

Gly Gly Asp Pro Glu Val Arg Lys Gln Met Pro Pro Pro Pro Cys
                405                 410                 415

Pro Gly Arg Glu Leu Phe Asp Asp Pro Ser Tyr Val Asn Val Gln Asn
                420                 425                 430

Leu Asp Lys Ala Arg Gln Ala Val Gly Ala Gly Pro Pro Asn Pro
        435                 440                 445

Ala Ile Asn Gly Ser Ala Pro Arg Asp Leu Phe Asp Met Lys Pro Phe
    450                 455                 460

Glu Asp Ala Leu Arg Val Pro Pro Pro Gln Ser Val Ser Met Ala
465                 470                 475                 480

Glu Gln Leu Arg Gly Glu Pro Trp Phe His Gly Lys Leu Ser Arg Arg
                485                 490                 495

Glu Ala Glu Ala Leu Leu Gln Leu Asn Gly Asp Phe Leu Val Arg Glu
            500                 505                 510

Ser Thr Thr Thr Pro Gly Gln Tyr Val Leu Thr Gly Leu Gln Ser Gly
            515                 520                 525

Gln Pro Lys His Leu Leu Val Asp Pro Glu Gly Val Val Arg Thr
        530                 535                 540

Lys Asp His Arg Phe Glu Ser Val Ser His Leu Ile Ser Tyr His Met
545                 550                 555                 560

Asp Asn His Leu Pro Ile Ile Ser Ala Gly Ser Glu Leu Cys Leu Gln
                565                 570                 575

Gln Pro Val Glu Arg Lys Leu Gly Gly Gly Ser Gly Gly Gly Gly
                580                 585                 590

Ser Leu Glu Ser Met Gly Val Ile Thr Asp Ser Leu Ala Val Val Ala
            595                 600                 605

Arg Thr Asp Arg Pro Ser Gln Gln Leu Arg Ser Leu Asn Gly Glu Trp
        610                 615                 620

Arg Phe Ala Trp Phe Pro Ala Pro Glu Ala Val Pro Glu Ser Trp Leu
625                 630                 635                 640

Glu Cys Asp Leu Pro Glu Ala Asp Thr Val Val Pro Ser Asn Trp
                645                 650                 655

Gln Met His Gly Tyr Asp Ala Pro Ile Tyr Thr Asn Val Thr Tyr Pro
                660                 665                 670

Ile Thr Val Asn Pro Pro Phe Val Pro Thr Glu Asn Pro Thr Gly Cys
            675                 680                 685

Tyr Ser Leu Thr Phe Asn Val Asp Glu Ser Trp Leu Gln Glu Gly Gln
        690                 695                 700

Thr Arg Ile Ile Phe Asp Gly Val Asn Ser Ala Phe His Leu Trp Cys
705                 710                 715                 720

Asn Gly Arg Trp Val Gly Tyr Gly Gln Asp Ser Arg Leu Pro Ser Glu
                725                 730                 735

Phe Asp Leu Ser Ala Phe Leu Arg Ala Gly Glu Asn Arg Leu Ala Val
            740                 745                 750

Met Val Leu Arg Trp Ser Asp Gly Ser Tyr Leu Glu Asp Gln Asp Met
        755                 760                 765

Trp Arg Met Ser Gly Ile Phe Arg Asp Val Ser Leu Leu His Lys Pro
770                 775                 780
```

-continued

```
Thr Thr Gln Ile Ser Asp Phe His Val Ala Thr Arg Phe Asn Asp Asp
785                 790                 795                 800

Phe Ser Arg Ala Val Leu Glu Ala Glu Val Gln Met Cys Gly Glu Leu
                805                 810                 815

Arg Asp Tyr Leu Arg Val Thr Val Ser Leu Trp Gln Gly Glu Thr Gln
            820                 825                 830

Val Ala Ser Gly Thr Ala Pro Phe Gly Gly Glu Ile Ile Asp Glu Arg
        835                 840                 845

Gly Gly Tyr Ala Asp Arg Val Thr Leu Arg Leu Asn Val Glu Asn Pro
    850                 855                 860

Lys Leu Trp Ser Ala Glu Ile Pro Asn Leu Tyr Arg Ala Val Val Glu
865                 870                 875                 880

Leu His Thr Ala Asp Gly Thr Leu Ile Glu Ala Glu Ala Cys Asp Val
                885                 890                 895

Gly Phe Arg Glu Val Arg Ile Glu Asn Gly Leu Leu Leu Leu Asn Gly
            900                 905                 910

Lys Pro Leu Leu Ile Arg Gly Val Asn Arg His Glu His His Pro Leu
        915                 920                 925

His Gly Gln Val Met Asp Glu Gln Thr Met Val Gln Asp Ile Leu Leu
    930                 935                 940

Met Lys Gln Asn Asn Phe Asn Ala Val Arg Cys Ser His Tyr Pro Asn
945                 950                 955                 960

His Pro Leu Trp Tyr Thr Leu Cys Asp Arg Tyr Gly Leu Tyr Val Val
                965                 970                 975

Asp Glu Ala Asn Ile Glu Thr His Gly Met Val Pro Met Asn Arg Leu
            980                 985                 990

Thr Asp Asp Pro Arg Trp Leu Pro Ala Met Ser Glu Arg Val Thr Arg
        995                 1000                1005

Met Val Gln Arg Asp Arg Asn His Pro Ser Val Ile Ile Trp Ser
    1010                1015                1020

Leu Gly Asn Glu Ser Gly His Gly Ala Asn His Asp Ala Leu Tyr
    1025                1030                1035

Arg Trp Ile Lys Ser Val Asp Pro Ser Arg Pro Val Gln Tyr Glu
    1040                1045                1050

Gly Gly Gly Ala Asp Thr Thr Ala Thr Asp Ile Ile Cys Pro Met
    1055                1060                1065

Tyr Ala Arg Val Asp Glu Asp Gln Pro Phe Pro Ala Val Pro Lys
    1070                1075                1080

Trp Ser Ile Lys Lys Trp Leu Ser Leu Pro Gly Glu Thr Arg Pro
    1085                1090                1095

Leu Ile Leu Cys Glu Tyr Ala His Ala Met Gly Asn Ser Leu Gly
    1100                1105                1110

Gly Phe Ala Lys Tyr Trp Gln Ala Phe Arg Gln Tyr Pro Arg Leu
    1115                1120                1125

Gln Gly Gly Phe Val Trp Asp Trp Val Asp Gln Ser Leu Ile Lys
    1130                1135                1140

Tyr Asp Glu Asn Gly Asn Pro Trp Ser Ala Tyr Gly Gly Asp Phe
    1145                1150                1155

Gly Asp Thr Pro Asn Asp Arg Gln Phe Cys Met Asn Gly Leu Val
    1160                1165                1170

Phe Ala Asp Arg Thr Pro His Pro Ala Leu Thr Glu Ala Lys His
    1175                1180                1185

Gln Gln Gln Phe Phe Gln Phe Arg Leu Ser Gly Gln Thr Ile Glu
```

-continued

```
            1190                1195                1200
Val Thr Ser Glu Tyr Leu Phe Arg His Ser Asp Asn Glu Leu Leu
    1205                1210                1215
His Trp Met Val Ala Leu Asp Gly Lys Pro Leu Ala Ser Gly Glu
    1220                1225                1230
Val Pro Leu Asp Val Ala Pro Gln Gly Lys Gln Leu Ile Glu Leu
    1235                1240                1245
Pro Glu Leu Pro Gln Pro Glu Ser Ala Gly Gln Leu Trp Leu Thr
    1250                1255                1260
Val Arg Val Val Gln Pro Asn Ala Thr Ala Trp Ser Glu Ala Gly
    1265                1270                1275
His Ile Ser Ala Trp Gln Gln Trp Arg Leu Ala Glu Asn Leu Ser
    1280                1285                1290
Val Thr Leu Pro Ala Ala Ser His Ala Ile Pro His Leu Thr Thr
    1295                1300                1305
Ser Glu Met Asp Phe Cys Ile Glu Leu Gly Asn Lys Arg Trp Gln
    1310                1315                1320
Phe Asn Arg Gln Ser Gly Phe Leu Ser Gln Met Trp Ile Gly Asp
    1325                1330                1335
Lys Lys Gln Leu Leu Thr Pro Leu Arg Asp Gln Phe Thr Arg Ala
    1340                1345                1350
Pro Leu Asp Asn Asp Ile Gly Val Ser Glu Ala Thr Arg Ile Asp
    1355                1360                1365
Pro Asn Ala Trp Val Glu Arg Trp Lys Ala Ala Gly His Tyr Gln
    1370                1375                1380
Ala Glu Ala Ala Leu Leu Gln Cys Thr Ala Asp Thr Leu Ala Asp
    1385                1390                1395
Ala Val Leu Ile Thr Thr Ala His Ala Trp Gln His Gln Gly Lys
    1400                1405                1410
Thr Leu Phe Ile Ser Arg Lys Thr Tyr Arg Ile Asp Gly Ser Gly
    1415                1420                1425
Gln Met Ala Ile Thr Val Asp Val Glu Val Ala Ser Asp Thr Pro
    1430                1435                1440
His Pro Ala Arg Ile Gly Leu Asn Cys Gln Leu Ala Gln Val Ala
    1445                1450                1455
Glu Arg Val Asn Trp Leu Gly Leu Gly Pro Gln Glu Asn Tyr Pro
    1460                1465                1470
Asp Arg Leu Thr Ala Ala Cys Phe Asp Arg Trp Asp Leu Pro Leu
    1475                1480                1485
Ser Asp Met Tyr Thr Pro Tyr Val Phe Pro Ser Glu Asn Gly Leu
    1490                1495                1500
Arg Cys Gly Thr Arg Glu Leu Asn Tyr Gly Pro His Gln Trp Arg
    1505                1510                1515
Gly Asp Phe Gln Phe Asn Ile Ser Arg Tyr Ser Gln Gln Gln Leu
    1520                1525                1530
Met Glu Thr Ser His Arg His Leu Leu His Ala Glu Glu Gly Thr
    1535                1540                1545
Trp Leu Asn Ile Asp Gly Phe His Met Gly Ile Gly Gly Asp Asp
    1550                1555                1560
Ser Trp Ser Pro Ser Val Ser Ala Glu Phe Gln Leu Ser Ala Gly
    1565                1570                1575
Arg Tyr His Tyr Gln Leu Val Trp Cys Gln Lys
    1580                1585
```

```
<210> SEQ ID NO 2
<211> LENGTH: 42
<212> TYPE: PRT
<213> ORGANISM: Artificial
<220> FEATURE:
<223> OTHER INFORMATION: Enzyme fragment

<400> SEQUENCE: 2

Asp Ser Leu Ala Val Val Leu Gln Arg Arg Asp Trp Glu Asn Pro Gly
1               5                   10                  15

Val Thr Gln Leu Asn Arg Leu Ala Ala Arg Pro Pro Phe Ala Ser Trp
                20                  25                  30

Arg Asn Ser Glu Glu Ala Arg Thr Asp Arg
                35                  40
```

RECEPTOR TYROSINE KINASE ASSAYS

CROSS-REFERENCE TO RELATED APPLICATIONS

This application claims priority from U.S. Provisional Patent Application No. 61/089,799, filed Aug. 18, 2008, which is hereby incorporated by reference in its entirety.

STATEMENT OF GOVERNMENTAL SUPPORT

None.

REFERENCE TO SEQUENCE LISTING, COMPUTER PROGRAM, OR COMPACT DISK

Applicants assert that the paper copy of the Sequence Listing is identical to the Sequence Listing in computer readable form found on the accompanying computer file. Applicants incorporate the contents of the sequence listing by reference in its entirety.

BACKGROUND OF THE INVENTION

1. Field of the Invention

The field of this invention is the determination of phosphorylation of tyrosine on a receptor tyrosine kinase and screening of compounds that affect the phosphorylation.

2. Background

Presented below is background information on certain aspects of the present invention as they may relate to technical features referred to in the detailed description, but not necessarily described in detail. These materials may be consulted for specific language, which may be omitted from the present specification and are, as stated in the Conclusion, incorporated by reference. The discussion below should not be construed as an admission as to the relevance of the information to the appended claims or the prior art effect of the material described.

Pharmaceutical small molecule drug discovery is predicated on discovering compounds that bind to receptors or cytosolic proteins and act as agonists, antagonists, inverse agonists or modulators. One important class of proteins known as receptor tyrosine kinases ("RTKs") are attractive targets, as these proteins act to induce a number of disease associated pathways. An important focus of pharmaceutical drug discovery is the identification of surrogate ligands for proteins, e.g., receptors, kinases, or other proteins in the pathway of phosphorylation. Of particular interest in this respect is a subclass of cell surface receptor proteins known as receptor tyrosine kinases. Another important class of proteins is the cytosolic kinases, which can phosphorylate one or a plurality of RTKs. By activating or inhibiting these kinases, one can inhibit the activation of the RTK target of the cytosolic kinase.

The RTK family functions in the regulation of cell growth, cell differentiation, adhesion, migration and apoptosis (Blume-Jensen and Hunter 2001 *Nature* 411:355-65) (Ullrich and Schlessinger 1990 *Cell* 61:203-12) (Schlessinger 2000 *Cell* 103:211-25) (Hubbard and Till 2000 *Annu Rev Biochem* 69:373-98). A number of human diseases have been linked to alterations in RTKs (Akin and Metcalfe 2004 *J Allergy Clin Immunol* 114:13-9) (Verheul and Pinedo 2003 *Drugs Today* (Barc) 39 Suppl C: 81-93) (Corfas et al., 2004 *Nat Neurosci* 7:575-80). Many RTKs have been identified as oncogenes in transforming retrovirus or human cancers (Hunter 2000 *Cell* 100:113-27) (Shawver et al., 2002) (Muller-Tidow et al., 2004), and recent reports indicate that RTKs may play a critical role in almost all types of human cancer (Shawver et al., 2002 *Cancer Cell* 1:117-23) (Prenzel et al., 2000 *Breast Cancer Res* 2:184-90) (Mass 2004 *Int J Radiat Oncol Biol Phys* 58:932-40). Both naturally occurring and artificial ligands that modulate RTK activity and signaling thus would be of tremendous interest from a therapeutic standpoint with respect to cancer and other diseases. (Haluska and Adjei 2001 *Curr Opin Investig Drugs* 2:280-6) (Sawyer et al., 2003 *BioTechniques* Suppl:2-10, 12-5). The ability to quickly, efficiently, and effectively screen vast libraries of compounds for particular activities has become a goal of the pharmaceutical industry. Desirably, the methods provide more than just binding information, frequently employing whole cells, where biological processes occur in relation to the compounds being screened.

Many cytokine receptors do not possess intrinsic kinase activity. However, they also initiate intracellular cascades of tyrosine phosphorylation. To do this they interact with separate proteins that are in the cytosol termed non-receptor tyrosine kinases (NRTK's). These proteins, such as the JAK kinases, bind to the intracellular domain of cytokine receptors. Once the cytokine receptor binds ligand and oligomerizes, this brings the JAK proteins into close proximity initiating trans-phosphorylation (by the JAK proteins) of the JAK proteins and the associated receptor.

High throughput screening has become a commonly employed strategy to identify novel compounds with particular activities from a diverse chemical library of compounds. Often, high throughput screening assays are either based upon measuring compound binding to defined molecular targets or measuring functional outputs resulting from compound/receptor interactions. However, both binding assays and functional assays have limitations. For example, for various technical reasons, binding assays are preformed in non-physiological conditions. Artificial, non-physiological conditions may impact and influence receptor pharmacology, leading to increased unreliability and difficulty in accurate interpretation of the data. Another drawback arises from the nature of the assay, which measures receptor binding only. Thus, binding competition assays do not provide information regarding the physiological function of ligands, such as whether the ligand functions as an agonist or antagonist. Since the only information obtained is binding, where the binding need not be at the target site, there can be many false positives.

Functional assays overcome many of the limitations associated with binding competition assays. Normally, cells are employed, which have the capability to respond to agonist binding as part of the assay protocol Therefore, the assays can provide a measure of the activity resulting from binding and allow for activity/concentration determinations. With the assay being performed under physiological conditions within the cell, one obtains results that more closely approximate the results that may be anticipated in vivo.

Several functional assays have been described for receptor tyrosine kinases. Exemplary assays include the quantification of autophosphorylation of RTKs (Olive 2004 *Expert Rev Proteomics* 1:327-41), measurement of phosphorylation of RTKs and downstream signaling molecules (ibid), measurement of intracellular calcium release (Dupriez et al., 2002 *Receptors Channels* 8:319-30), or measurement of RTK dependent cell proliferation (Mosmann 1983 *J Immunol Methods* 65:55-63) (Bellamy 1992 *Drugs* 44; 690-708). Despite the substantial variety of assays that have been developed for evaluating ligands for RTKs, there is still a substantial need for additional assays that can provide advantages as to the nature of the protocol, the involvement of the technician in performing the assay, the number of steps that can lead to errors in the result, the choice of equipment, the effect of organic solvents, the dynamic range and the sensitivity of the assay.

Relevant Patent Literature

U.S. patents and applications include U.S. Pat. Nos. 5,667,980; 5,773,237; 5,976,893; a group of patents with the same disclosure U.S. Pat. Nos. 5,891,650, 5,914,237, 6,025,145, and 6,287,784; 6,413,730, 2004/0038298, 2004/0161787; 2006/0199226; and 2008/0103107.

SUMMARY OF THE INVENTION

Mammalian cells are provided comprising at least two genetic expression constructs: a first construct of an RTK fused to a first member of a pair of fragments of β-galactosidase; a second construct of a polypeptide, ("a phosphotyrosine binding peptide") that binds to the phosphorylated RTK fused to the second fragment of β-galactosidase; and as appropriate, a third construct expressing a cytosolic kinase phosphorylating tyrosine receptor kinases. Upon stimulation of the RTK, the expression product of the second construct binds to the phosphorylated RTK bringing the two fragments into proximity to form an active β-galactosidase, where phosphorylation may result from the RTK or the cytosolic kinase. The two fragments have a low affinity for each other, so that there is relatively low formation of β-galactosidase in the absence of the binding of the two expression products. Addition of a substrate for the β-galactosidase that produces a detectable product provides a readout related to the degree of binding of the two expression products. Examples of these peptides and kinases are given below.

DESCRIPTION OF THE SPECIFIC EMBODIMENTS

Figure 1:
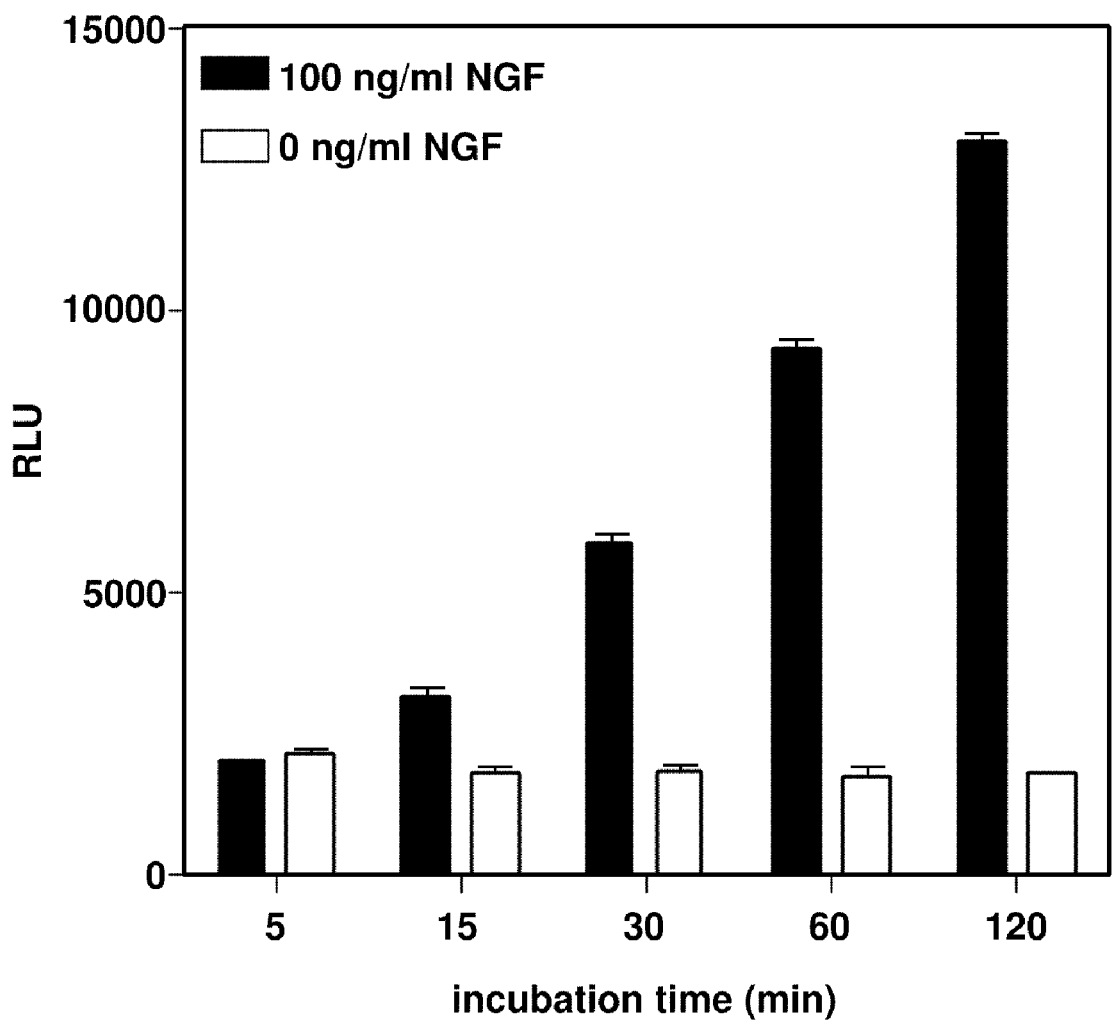
FIG. 1 is a bar graph of the response in U2OS cells of Tropomyosin-Related Kinase A fused to a low affinity small fragment of β-galactosidase (TrkA-PK) and Src Homology 2 containing transforming protein 1 fused to a complementary β-galactosidase fragment (SHC1-EA) to the addition of Nerve Growth Factor (NGF); It shows that Activation of TrkA-PK in U2OS cells causes recruitment of SHC1-EA phosphotyrosine binding peptide resulting in increased enzyme activity. U2OS cells expressing the TrkA-PK and SHC1-EA fusion proteins were plated at 10K/well in each well of a 384-well plate in serum-free medium with 0.1% FBS. The next day, the cells were treated with 100 ng/ml NGF or PBS+1% BSA for different time periods at room temperature and assayed using PathHunter Detection reagent.

Methods are provided for determining the phosphorylation of RTKs. Double or treble stable transformed cells are employed comprising two, and optionally a third, expression constructs: (1) a fusion of an RTK with a member of an enzyme fragment pair at the cytosolic C-terminus of the RTK; (2) a polypeptide sequence that binds to the phosphorylated RTK (a phosphotyrosine binding domain) fused to the complementary member of the enzyme fragment pair; and where the RTK does not auto-phosphorylate, (3) a non-receptor tyrosine kinase, generally with a strong promoter for over expression. The enzyme pair is derived from β-galactosidase, where the fragments are relatively unable to independently complex to form an active enzyme, namely having a weak affinity for each other, but able to form an active β-galactosidase when the proteins bind together to which the fragments are fused.

In performing the method, the cells are grown in an appropriate medium. The cells are seeded in basal media with Bovine Serum Albumin (BSA), using commonly employed conditions. For determining whether a candidate compound is an agonist or inverse agonist, the putative agonist is added and the cells incubated for a sufficient time for a reaction to occur. For determining whether a candidate compound is an antagonist, the cells are first incubated with the putative antagonist for sufficient time for the antagonist to bind, followed by the addition of an agonist and incubation for sufficient time for a reaction to occur. For determination of whether a candidate compound is a modulator, cells are first incubated with a limiting concentration of either an agonist or antagonist, followed by incubation with the proposed modulator to assess a change in the response. A commercially available β-galactosidase substrate is then added that provides a detectable signal, the substrate optionally combined with a lysing agent, and the signal detected as a measure of the binding activity of the agonist or antagonist.

The media will be conventional for the particular cells used; F-12 for CHO cells, modified Eagle's media for U2OS cells, standard DMEM for HEK cells, etc. Conveniently, the assays are performed in microtiter well plates, where the volumes may vary from about 4 to 100 µl, more usually 10 to 25 µl. Generally, about 2 to $20\times10^3$ cells per 10 µl are employed in the assay, more usually 3 to $10\times10^3$ cells per 10 µl are employed in the assay.

Temperatures will generally range from about 10 to 40° C. With the agonist assay, ambient temperatures are convenient, while with the antagonist assay, physiologic temperature (37° C.) is convenient. The incubation times employed with the ligands are to provide for a robust result, generally ranging from about 5 min to 2 h, more usually from about 10 min to 1 h, where the ligand has sufficient time to bind to the RTK, phosphorylation to occur and binding of the PTB-comprising-protein to the phosphorylated RTK in sufficient number to occur. (By PTB is intended all phosphotyrosine binding domains including domains referred to as phosphotyrosine domains, SH2 domains, artificially engineered domains, single chain, e.g., Fab, antibodies, and the like.) The precise time employed for achieving at least substantial optimization can be determined empirically.

With a β-galactosidase substrate able to cross the cell membrane, the substrate is added as a dissolving solid or in a solution. Alternatively, the reagent solution may provide for permeabilizing or lysis of the cells and release of any complex formed in the cell to the assay medium. Any conventional lysis buffer may be employed that does not interfere with the β-galactosidase reaction with its substrate. Various ionic buffers, such as CHAPS, may be employed at 1-5%, generally not more than 3%, in a convenient buffer, such as PBS or HEPES, where numerous other substitutes are known in the field. The reagent solution will generally be about 0.5-2 times the volume of the assay medium. After addition of the β-galactosidase substrate, the solution will usually be incubated for from 5-200 min, usually 10-150 min and the signal read. The temperature will generally be at the temperature of the incubation medium or conveniently in the range of about 20-40° C.

The β-galactosidase substrate will provide a fluorescent or luminescent product. A fluorescent or chemiluminescent reader, respectively, is then used to read the signal. Desirably a luminescent reagent and optionally a signal enhancer are employed. The luminescent reagent will be in large excess in relation to the maximum amount of β-galactosidase that is likely to be formed. Conveniently, a luminescent substrate is used, available as Galacton Star from ABI in conjunction with the Emerald II enhancer. Any equivalent luminescent substrate composition may be employed. The substrate will be present in about 1 to 10 weight percent, while the enhancer will be present in about 10 to 30 weight percent of the reagent solution. These amounts will vary depending upon the particular substrate composition employed. The reagent solution may be prepared as a 5-20× concentrate or higher for sale or the solids may be provided as powders and dissolved in water at the appropriate proportions.

Standards will usually be used, whereby the signal is related to the concentration of a known stimulator performed under the same conditions as the candidate compound. A graph can be prepared that shows the change in signal with the change in concentration of the standard compound. The assay is sensitive to $EC_{50}$s of not greater than nanomolar of candidate compound, generally sensitive to less than about 1 µM, in most cases sensitive to less than about 500 nM, frequently sensitive to less than 100 nM and can in many cases detect $EC_{50}$s of less than 50 nM. The S/B (signal/background) ratios are generally are at least about 2 fold, more usually at least about 3 fold, and can be greater than about 50 fold.

Instead of screening compounds for agonist or antagonist activity, e.g., an active ligand, one can screen physiological or other samples for ligand activity, namely as a diagnostic tool. A sample is used in place of the candidate compound and the assay is performed in the same way. Physiological samples may include blood, plasma, saliva, CSF, tissue, lysed cells, etc. The sample may be subject to prior treatment, such as filtration, centrifugation, citration, heating, precipitation, etc. The amount of sample will depend upon the anticipated level of the agonist or antagonist. The subject method has the advantage over an immunoassay in measuring only components that actively bind the RTK rather than epitopic sites of the components.

For convenience kits can be provided. In the subject assays, the EA fusion protein may be provided as a construct for expression of EA to be introduced into the cell or cells may be provided that are appropriately modified to provide EA in the cell. Generally, the kits would include an insert with instructions for performing the assay. The instructions may be printed or electronic, e.g., a CD or floppy disk. The kits find use in marketing the product and encouraging the use of the assay for research and commercial settings.

Various, known cell lines may be employed for the assay. Cell lines that find use include U2OS, CHO, HeLa, HepG2, HEK, and the like.

The RTKs may be divided into self-phosphorylating receptors and receptors that require an independent kinase, where a large number of cytosolic kinases are known that have a relatively narrow repertoire of RTKs that each phosphorylates when the RTK is activated. Therefore, the subject assays allow for the investigation of activity of compounds that are ligands for the RTKs or activators or inhibitors of cytosolic kinases, where the RTKs that are phosphorylated by the cytosolic kinase are known There are a large number of RTKs that initiate a number of different pathways and new RTKs are likely to be discovered. The RTKs have been divided into a number of classes as follows: RTK class I (EGF receptor family); II (insulin receptor family); III (PDGR receptor family); IV (FGF receptor family); V (VEGF receptor family); VI (HGF receptor family); VII (Trk receptor family); VIII (AXL receptor family); IX (AXL receptor family); X (LTK receptor family); XI (TIE receptor family); XII (ROR receptor family); XIII (DDR receptor family); XV (KLG receptor family); XVI (RYK receptor family); and XVII (MuSK receptor family).

Each of the RTKs binds to one or more polypeptides having phosphotyrosine binding ("PTB") domains. A large class of proteins have what is referred to as the SH2 (Src homology 2) domain. These proteins include Abl, GRB2, RasGAP, STAT proteins, ZAP70, SHP2, PI3K, Phospholipase C γ form, CRK, SOCS, Shc, and Src. Other proteins include FRS2, FE65, Xll/MINT, NUMB, EPS8, RGS12, DAB, ODIN, JIP-1, ARH and ICAP1. (Further information on these proteins may be found by searching for symbols that contain these abbreviations, as given in Pubmed and/or at genenames.org/cgi-bin/hgnc_search.pl.) Complete sequence information and annotations of the gene symbols used here may also be obtained by those skilled in the art from OMIM or Swiss-Prot.

The PTB proteins need not be from the same species as the RTK, so long as they have a sufficient binding affinity to provide for a robust assay. The entire PTB protein need not be used, so long as the fragment that is employed comprises the PTB domain and has the desired level of affinity for the RTK phosphotyrosine site.

The RTKs that depend upon cytosolic receptors include T and B-cell receptors, integrins, interferon receptors, interleukin receptors, GP130 associated proteins, etc. Among the families of receptors that find application in the subject invention, the following are illustrative. Single chain: EPOR, GHR, CFSR, PRLR, MPL; IFN Family: IFNAR1, 2, IFNGR1, 2; γC Family: IL2RA, B, G, IL4R, IL2RG (Type 1 receptor), IL4R-IL13RA1 (Type II receptor), IL7R, IL2RG, IL9R, IL15RA, IL2RB, IL10RA, B, IL12RB1, 2, IL13RA1; IL3 Family: IL3RA, CSF2RA, B, IL5RA, GP130 Family: IL6R, IL6ST, IL11RA, LIFR, OSMR, IL6GT, CNTFR, IL6ST, and LIFR.

Where a wild-type cytosolic kinase (NRTK) is not endogenously available and is required for phosphorylation, in addition to the RTKs indicated immediately above and the polypeptides having a PTB domain, there will also be expression of an exogenously introduced wild-type NRTK with a strong promoter to provide over expression of the NRTK. The overexpression can be determined empirically, but will usually provide a level of the NRTK in substantial excess, 2-fold or more, of the level of the NRTK present.

Typically individual plasmids are employed each with its own antibiotic resistance gene, except where one of the components is multiunit, the units may be on the same vector, e.g., plasmid. The vectors are introduced into the cells sequentially or simultaneously and the transformed cells selected by means of their antibiotic resistance. In order to facilitate the process bicistronic vectors may be used that include internal ribosome entry sites, such that both receptor subunits can be expressed from the same vector.

The detection system is dependent upon the use of β-galactosidase enzyme fragment complementation. In this system a small fragment of β-galactosidase and a larger fragment of β-galactosidase are employed, where the two fragments have a low affinity for each other. The small fragment of β-galactosidase ("ED") may have the naturally occurring sequence or a mutated sequence. Of particular interest are small fragments of from about 36 to 60, more usually not more than 50, amino acids. Desirably, the ED has a low affinity for the large fragment of β-galactosidase ("EA), so that there is little complexation between the large and small fragments in the absence of binding of the RTK and PTB peptides. For further description of the small fragments, see U.S. Pat. No. 7,135,325. For further description of mutated EDs, see U.S. patent application publication no. 2007/0275397, both of which references are incorporated herein in their entirety as if set forth herein. The small EDs and mutated EDs will generally have less than about 0.5, but at least about 0.1, of the activity of the wild-type sequence in the assay of interest or an analogous assay, while having less than about 60% of the conventionally used commercial sequence of about 90 amino acids in the absence of being fused to other proteins. For increasing affinity between the ED and EA, the longer EDs will be used and free of mutations from the wild-type sequence. One can determine empirically for a specific assay the desirable level of affinity of the two fragments, having a higher affinity when the affinity for the PTB peptide for the RTK is low.

Two expression constructs, and optionally a third, are employed: a fusion of one β-galactosidase fragment with the RTK, usually the small fragment; a fusion of the other β-galactosidase fragment with the PTB peptide, usually the large fragment; and optionally, an expression construct for an appropriate cytosolic kinase, particularly with a strong promoter. Conveniently, each protein is expressed from a different plasmid, with each plasmid having its own antibiotic resistance gene. Where the receptor is composed of multiple subunits, each encoded by a separate gene, conveniently, one may express more than one protein per plasmid using multiple promoters or bicistronic vectors or IRES.

For expression constructs and descriptions of other conventional manipulative processes, see, e.g., Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The gene encoding the fusion protein will be part of an expression construct. The gene is positioned to be under transcriptional and translational regulatory regions functional in the cellular host. The regulatory region may include an enhancer, which may provide such advantages as limiting the type of cell in which the fusion protein is expressed, requiring specific conditions for expression, naturally being expressed with the protein, and the like. In many instances, the regulatory regions may be the native regulatory regions of the gene encoding the protein, where the fusion protein may replace the native gene, may be in addition to the native protein, either integrated in the host cell genome or non-integrated, e.g., on an extrachromosomal element.

As indicated, the β-galactosidase fragment joined to the RTK will be fused at the C-terminus of the RTK, generally linked through a linker that conveniently has from 1 to 2 GGGS units. The large fragment fused to the PTB peptide may be fused directly to the peptide terminus, either N- or C-terminus, or have a linker, the same or different from the small fragment linker.

The following examples are offered by way of illustration and not by way of limitation.

EXPERIMENTAL

All cells lines used were from DiscoveRx Corporation and express various RTKs tagged with PK (42aa, DSLAVVLQR-RDWENPGVTQLNRLAARPPFASWRNSEEARTDR) (SEQ ID NO: 2) in cells stably expressing SH2-EA (Large β-galactosidase fragment, Full length β-galactosidase deleted in amino acids 31-41).

EXAMPLE:

Amino acids 1-583=SHC1
Amino Acids 584-597=Linker
Amino Acids 598- 1589=Large β-galactosidase fragment (EA)

(SEQ ID NO: 1)
MDLLPPKPKYNPLRNESLSSLEEGASGSTPPEELPSPSASSLGPILPPLP

GDDSPTTLCSFFPRMSNLRLANPAGGRPGSKGEPGRAADDGEGIVGAAMP

DSGPLPLLQDMNKLSGGGGRRTRVEGGQLGGEEWTRHGSFVNKPTRGWLH

PNDKVMGPGVSYLVRYMGCVEVLQSMRALDFNTRTQVTREAISLVCEAVP

GAKGATRRRKPCSRPLSSILGRSNLKFAGMPITLTVSTSSLNLMAADCKQ

IIANHHMQSISFASGGDPDTAEYVAYVAKDPVNQRACHILECPEGLAQDV

ISTIGQAFELRFKQYLRNPPKLVTPHDRMAGFDGSAWDEEEEEPPDHQYY

NDFPGKEPPLGGVVDMRLREGAAPGAARPTAPNAQTPSHLGATLPVGQPV

GGDPEVRKQMPPPPPCPGRELFDDPSYVNVQNLDKARQAVGGAGPPNPAI

NGSAPRDLFDMKPFEDALRVPPPPQSVSMAEQLRGEPWFHGKLSRREAEA

LLQLNGDFLVRESTTTPGQYVLTGLQSGQPKHLLLVDPEGVVRTKDHRFE

SVSHLISYHMDNHLPIISAGSELCLQQPVERKLGGGGSGGGGSLESMGVI

TDSLAVVARTDRPSQQLRSLNGEWRFAWFPAPEAVPESWLECDLPEADTV

VVPSNWQMHGYDAPIYTNVTYPITVNPPFVPTENPTGCYSLTFNVDESWL

QEGQTRIIFDGVNSAFHLWCNGRWVGYGQDSRLPSEFDLSAFLRAGENRL

AVMVLRWSDGSYLEDQDMWRMSGIFRDVSLLHKPTTQISDFHVATRFNDD

FSRAVLEAEVQMCGELRDYLRVTVSLWQGETQVASGTAPFGGEIIDERGG

YADRVTLRLNVENPKLWSAEIPNLYRAVVELHTADGTLIEAEACDVGFRE

VRIENGLLLLNGKPLLIRGVNRHEHHPLHGQVMDEQTMVQDILLMKQNNF

NAVRCSHYPNHPLWYTLCDRYGLYVVDEANIETHGMVPMNRLTDDPRWLP

-continued
AMSERVTRMVQRDRNHPSVIIWSLGNESGHGANHDALYRWIKSVDPSRPV

QYEGGGADTTATDIICPMYARVDEDQPFPAVPKWSIKKWLSLPGETRPLI

LCEYAHAMGNSLGGFAKYWQAFRQYPRLQGGFVWDWVDQSLIKYDENGNP

WSAYGGDFGDTPNDRQFCMNGLVFADRTPHPALTEAKHQQQFFQFRLSGQ

TIEVTSEYLFRHSDNELLHWMVALDGKPLASGEVPLDVAPQGKQLIELPE

LPQPESAGQLWLTVRVVQPNATAWSEAGHISAWQQWRLAENLSVTLPAAS

HAIPHLTTSEMDFCIELGNKRWQFNRQSGFLSQMWIGDKKQLLTPLRDQF

TRAPLDNDIGVSEATRIDPNAWVERWKAAGHYQAEAALLQCTADTLADAV

LITTAHAWQHQGKTLFISRKTYRIDGSGQMAITVDVEVASDTPHPARIGL

NCQLAQVAERVNWLGLGPQENYPDRLTAACFDRWDLPLSDMYTPYVFPSE

NGLRCGTRELNYGPHQWRGDFQFNISRYSQQQLMETSHRHLLHAEEGTWL

NIDGFHMGIGGDDSWSPSVSAEFQLSAGRYHYQLVWCQK

RTK Fusions include: ErbB-1 (EGFR), ErbB-2, ErbB3, ErbB4, INSR, IGF1R, IRR, PDGFRA, PDGFRB, CSF-1R, C-Kit, FGFR1, FGFR2, FGFR3, FGFR4, Flt3, VEGFR1(Flt-1), VEGFR-2 (Flk-1/KDR), VEGFR-3 (Flt-4), C-Met, RON, TrkA, TrkB, TrkC, AXL, MER, SKY (TYRO3)(Dtk), LTK (TYK1), ALK, Tie-1, Tie-2, (TEK), DDR1, DDR2, MuSK, RET, EPHA1, EPHA2, EPHA3, EPHA4, EPHA5, EPHA6, EPHA7, EPHA8, EPHA9, EPHB1, EPHB2, EPHB3, EPHB4, EPHB5, EPHB6, CCK4 (PTK7), ROS, AATYK1, AATYK2, AATYK3, ROR1, and ROR2.

Cell lines include: U2OS containing TrkA-PK fusion and SHC1-EA, U2OS containing INSR (insulin receptor)-PK fusion and PLCG2 (Phospholipase C, gamma 2 (phosphatidylinositol-specific))-EA, U2OS containing IGF1R-PK (insulin like growth factor-1 receptor) and SHC1-EA, U2OS containing TrkB-PK fusion and SHC1-EA, TrkC-PK fusion and SHC1-EA, U2OS containing PDGFRB-PK fusion containing PLCG1 (Phospholipase C, gamma 1)-EA, U2OS containing PDGFRB-PK fusion containing Grb2 (Growth factor receptor-bound protein 2)-EA, U2OS containing PDGFRB-PK fusion containing PLCG2-EA, U2OS containing PDGFRB-PK fusion containing PTPN11 (protein tyrosine phosphatase, non-receptor type 11)-EA, U2OS containing PDGFRB-PK fusion containing SYK (spleen tyrosine kinase)-EA, ErbB4 (v-erb-a erythroblastic leukemia viral oncogene homolog 4)-PK fusion and Grb2 (Growth factor receptor-bound protein 2)-EA.

Generally, the expression constructs for the fusion proteins includes at least (in order of 5' to 3') a promoter, followed by the receptor or SH2 domain, followed by a linker, followed by either the EA or PK. For all assays, 10,000 cells per well were seeded in 20 μL media and incubated overnight in 0.1% BSA and appropriate basal media (F-12 or DMEM). For agonist assays, 5 μL compound was added to cells and incubated at room temperature. For antagonist assays, 5 μL 5× compound was added to cells and incubated at 37° C./5% $CO_2$ for 10 minutes, after which 5 μL 6× agonist was added and incubated for 60 minutes at room temperature. SH2-EA complex formation with the RTK was detected with 50% (v/v) of PathHunter® Detection Reagent (Dx 93-0001, PathHunter reagents are available from DiscoveRx, Corp., Fremont, Calif.) (Lysis buffer active ingredient 1% CHAPS, Emerald II™ and Galacton Star™ are from Applied Biosystems). Data was read on Packard Victor 2® or PerkinElmer ViewLux® readers or comparable instrumentation and analyzed using GraphPad Prism 4® analysis software.

U2OS cells expressing the TrkA-PK and SHC1-EA fusion proteins were plated at 10K cells/well in each well of a 384-well plate in serum-free medium with 0.1% FBS. The next day, the cells were treated with 100 ng/ml NGF in PBS+1% BSA or PBS+1% BSA for different time periods at room temperature and assayed using PathHunter (DiscoveRx) Detection reagent. The results are shown in FIG. 1.

Figure 2:
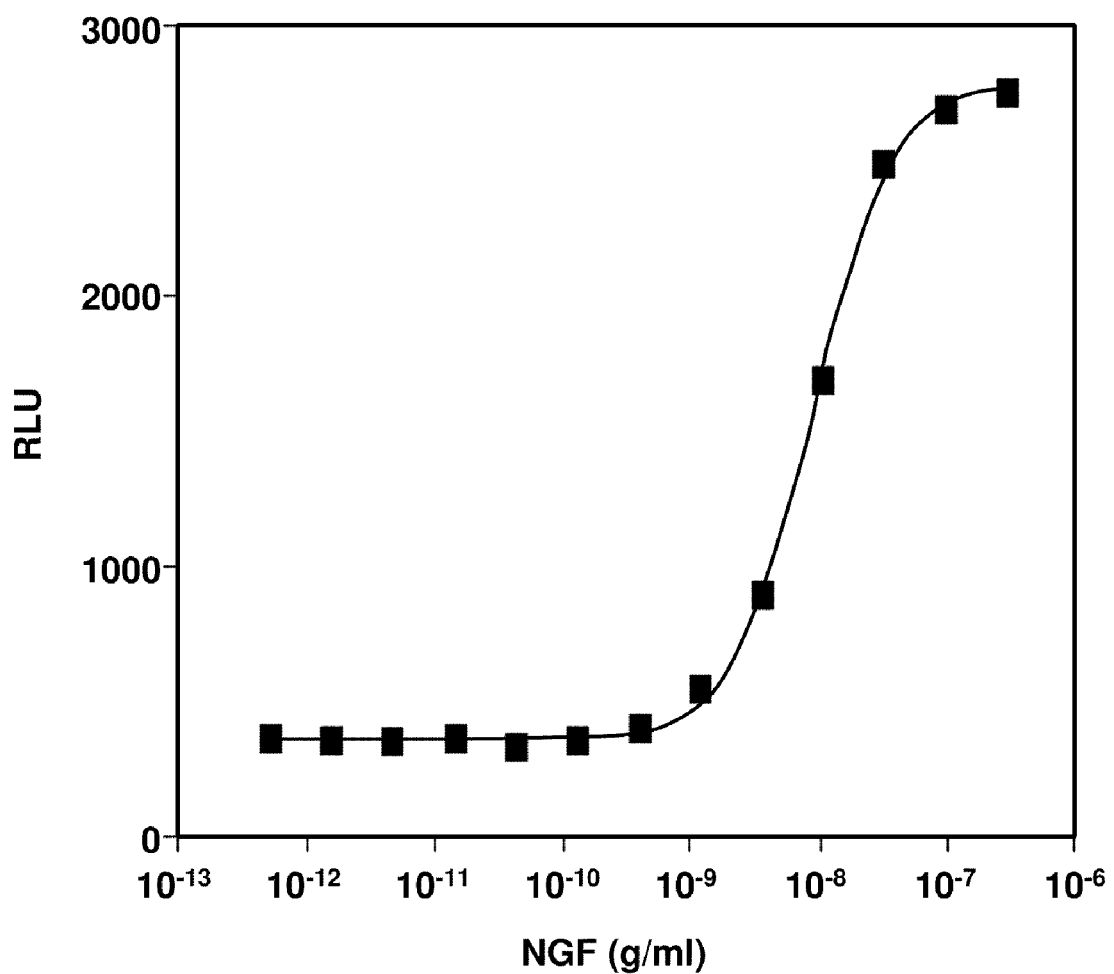
FIG. 2 is a graph of the dose response in U2OS cells of TrkA-PK and SHC1-EA to the addition of NGF. It shows that U2OS TRKA SHC1 cells show dose response to NGF. 5K/well U2OS TRKA SHC1 double-stable cells were plated in each well of a 384-well plate in serum-free medium with 0.1% FBS. The next day, the cells were treated with different concentrations of NGF for 1 hr at room temperature. Then PathHunter chemiluminescent substrate was added and the signal was read 1 hr later. EC50 of 9.3 ng/ml and an assay window of 7.8 were obtained.

5K cells/well U2OS TrkA-PK SHC1-EA double-stable cells were plated in each well of a 384-well plate in serum-free medium with 0.1% FBS. The next day, the cells were treated with different concentrations of NGF for 1 hr at room temperature (see above). Then PathHunter chemiluminescent substrate was added and the signal was read 1 hr later. $EC_{50}$ of 9.3 ng/ml and an assay window of 7.8 were obtained. The results are reported in FIG. 2.

Figure 3:
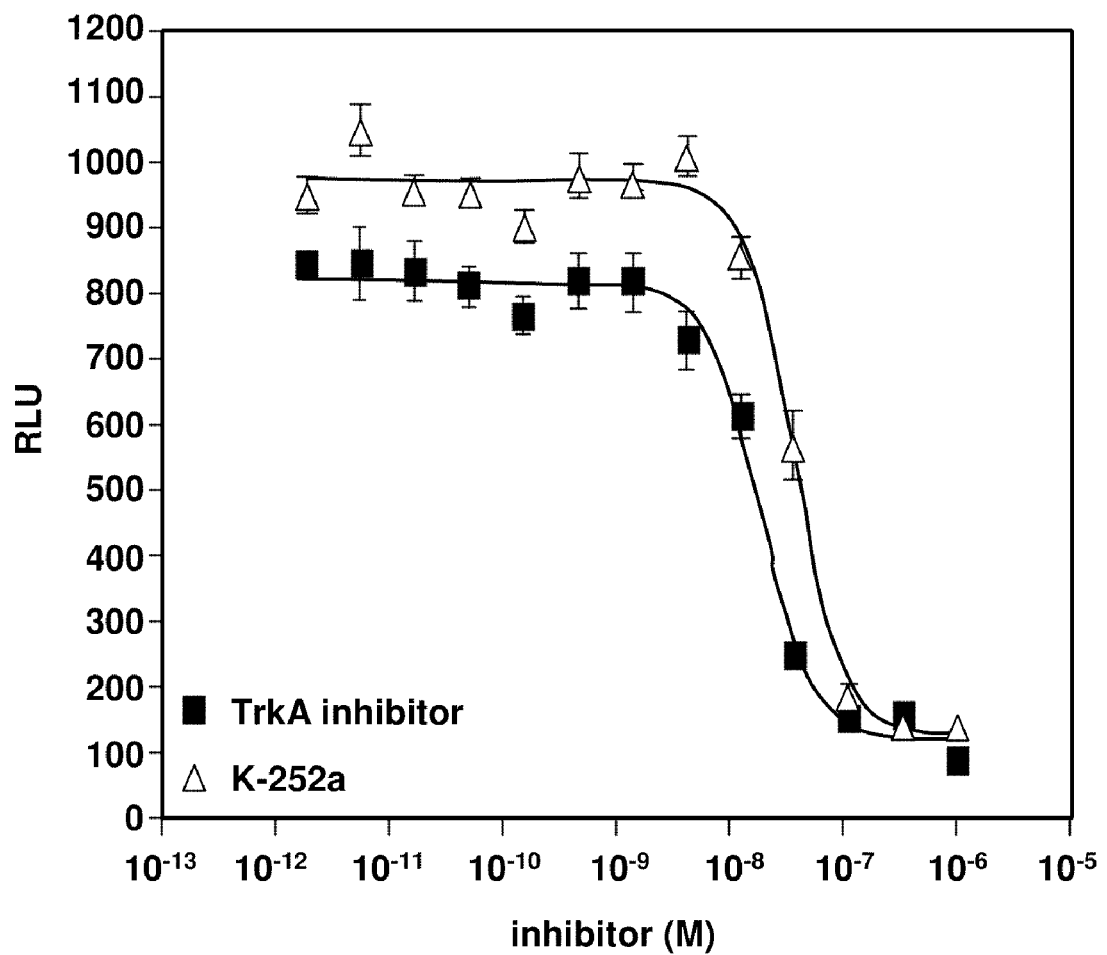
FIG. 3 is a graph of the dose response resulting from inhibitors added to U2OS cells of TrkA-PK and SHC1-EA followed by the addition of NGF. It shows that TRK inhibitors inhibit NGF stimulated assay signal. 5K/well U2OS TRKA SHC1 double-stable cells were plated in each well of a 384-well plate in serum-free medium with 0.1% FBS. The next day, the cells were treated with different concentrations of TrkA inhibitor or K-252a for 10 min at room temperature followed by 20 ng/ml NGF stimulation for 1 hr at room temperature. Then PathHunter chemiluminescent substrate was added and the signal was read 1 hr later. TrkA inhibitor gave an IC50 of 18 nM and an assay window of 6.7. K-252a gave an IC50 of 37 nM and an assay window of 7.6.

5K cells/well U2OS TrkA-PK SHC1-EA double-stable cells were plated in each well of a 384-well plate in serum-free medium with 0.1% FBS. The next day, the cells were treated with different concentrations of antagonists, such as a commercially available TrkA inhibitor or the Trk inhibitor K252a [(8R*,9S*,11S*)-(−)-9-hydroxy-9-methoxycarbonyl-8-methyl-2,3,9,10-tetrahydro-8,11-epoxy-1H,8H,11H-2,7b,11a-triazadibenzo(a,g)cycloocta(cde)-trinden-1-one] for 10 min at room temperature followed by 20 ng/ml NGF stimulation for 1 hr at room temperature (see above). Then PathHunter chemiluminescent substrate was added and the signal was read 1 hr later. TrkA inhibitor gave an $IC_{50}$ of 18 nM and an assay window of 6.7. K-252a gave an $IC_{50}$ of 37 nM and an assay window of 7.6. The results are reported in FIG. 3.

Figure 4:
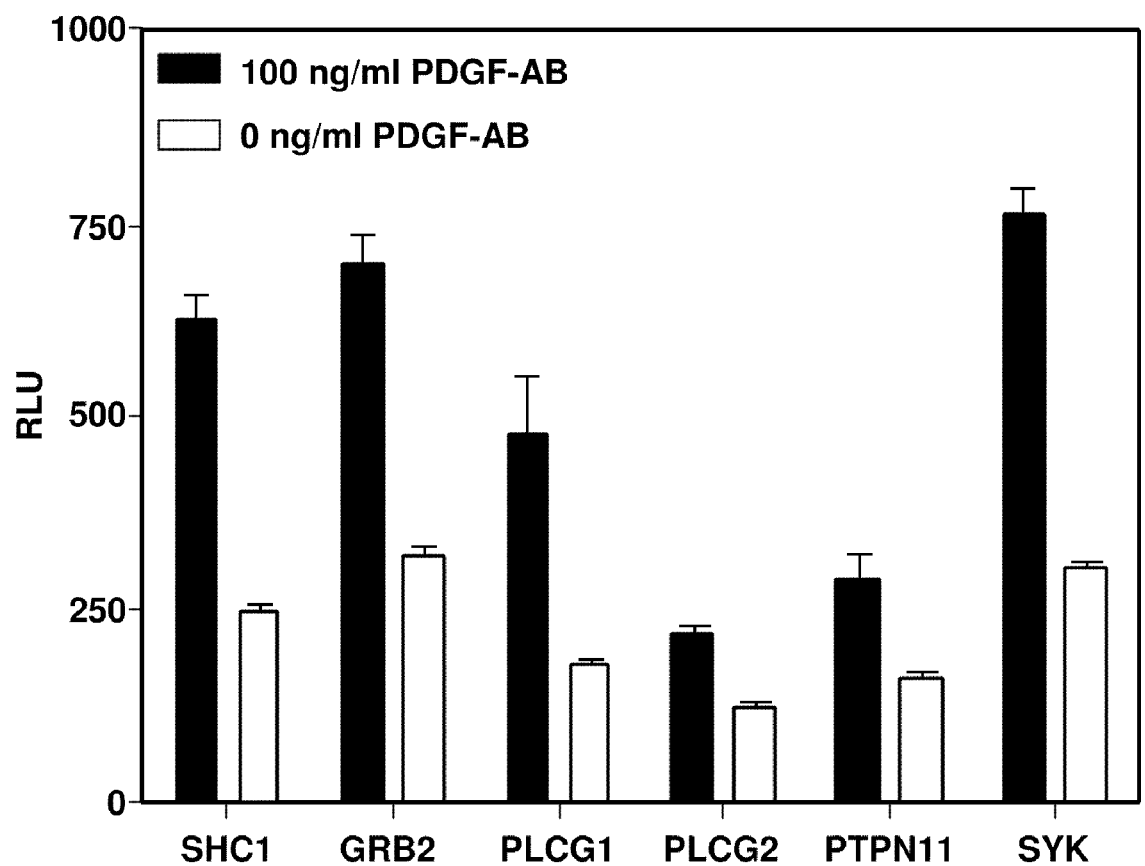
FIG. 4 is a bar graph of the dose response in U2OS of Platelet-Derived Growth Factor Receptor Beta fused to a low affinity small fragment of β-galactosidase (PDGFRB-PK) with different SH2 (Src Homology 2) domain-EA conjugates after treatment with Platelet Derived Growth Factor AB (PDGF-AB). It shows that PDGFRB interacts with different SH2 domain-containing cytoplasmic proteins (phosphotyrosine binding peptides). 5K/well PDGFRB-PK SH2-containing protein-EA double-stable cells were plated in each well of a 384-well. The next day, the cells were treated with (solid bars) or without (open bars) 100 ng/ml PDGF-AB for 1 hr at room temperature. Then PathHunter® chemiluminescent substrate was added and the signal was read 2 hrs later. (PathHunter® is a trademark of DiscoveRx Corporation, Fremont, Calif.)

5K cells/well PDGFRB-PK SH2-containing protein-EA double-stable cells were plated in each well of a 384-well plate in serum-free medium with 0.1% FBS. Six SH2-containing protein-EAs were used: SHC1-EA, Grb2-EA, PLCG-1-EA, PLCG2-EA, PTPN11-EA, and SYK-EA. The next day, the cells were treated with or without 100 ng/ml PDGF-AB in serum-free medium with 0.1% FBS for 1 hr at room temperature. Then PathHunter chemiluminescent substrate was added and the signal was read 2 hrs later. The results are reported in FIG. 4.

Figure 5:
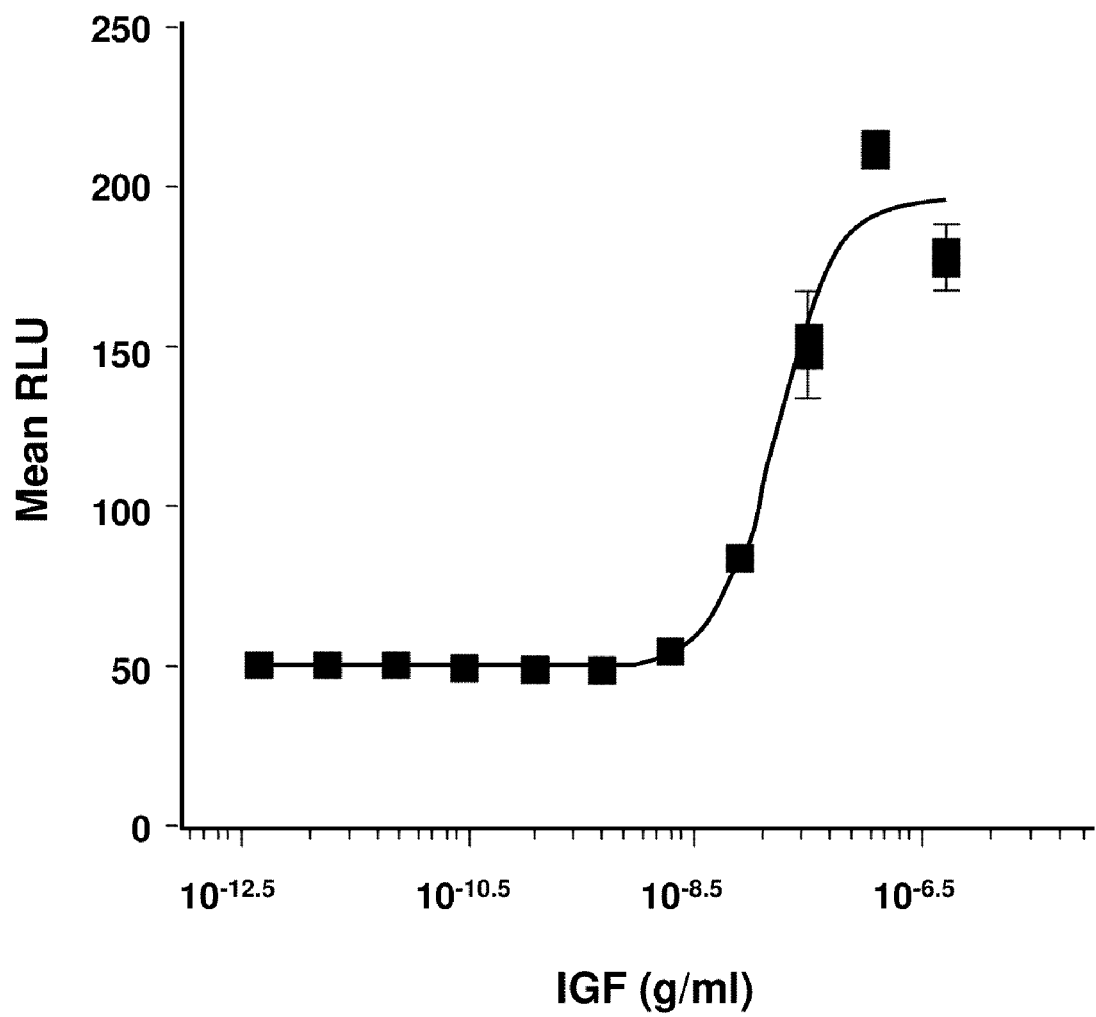
FIG. 5 is a graph of the dose response in U2OS cells of IGF1R fused to a low affinity small fragment of β-galactosidase (IGF1R-PK). Cells were plated in a 384-well plate at 10,000 cells/well, stimulated with IGF1 (Peprotech, Inc., Rocky Hill, N.J., Cat #/AF-100-11), a known ligand for IFG1R for 3 hours at room temperature according to the assay procedure provided. Following stimulation, detection reagents were added and signal was detected after 1 hour using the PathHunter® Detection Kit (93-0001). An assay window of 4.4 fold was observed and the EC50 for the ligand IGF1 was 17 ng/ml.
Figure 6:
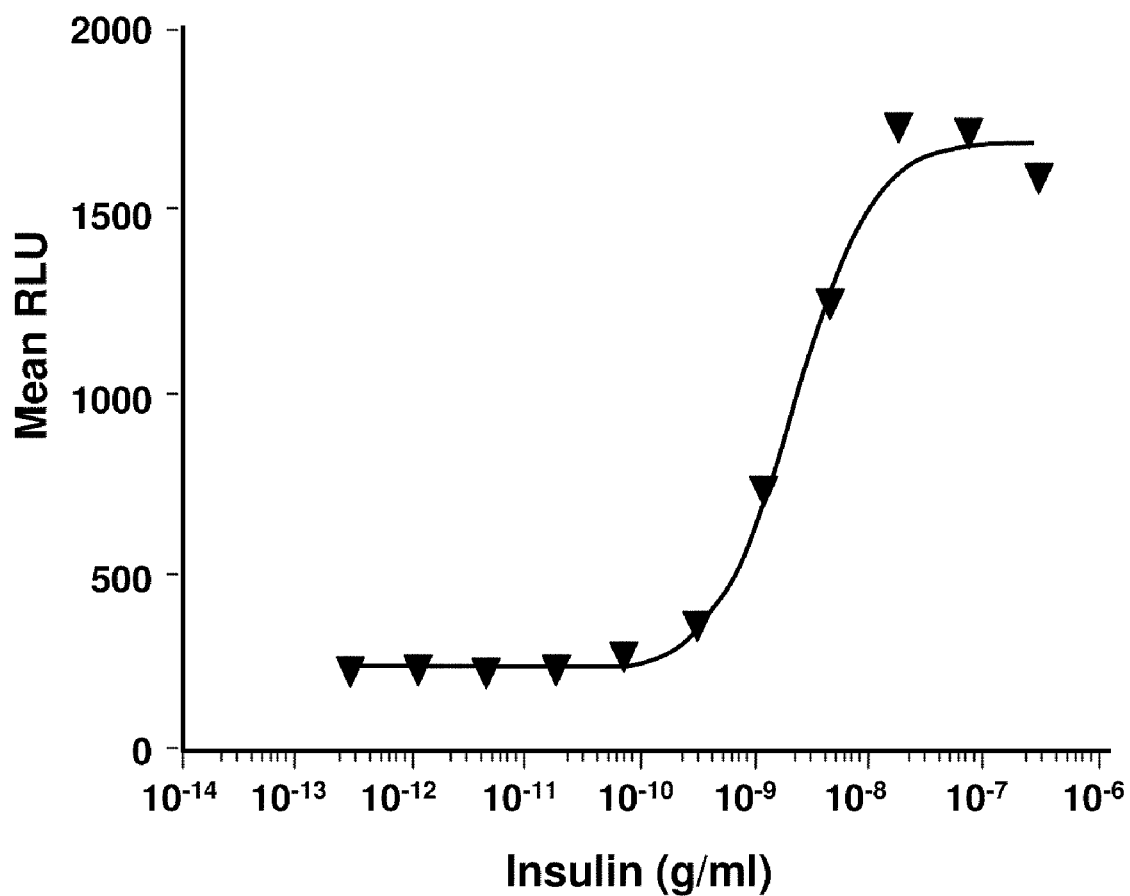
FIG. 6 is a graph of the dose response in U2OS cell of insulin receptor (INSR) fused to a low affinity small fragment of β-galactosidase (INSR-PK). Cells were plated in a 384-well plate at 10,000 cells/well, stimulated with insulin a known ligand for INSR, for 3 hours at room temperature according to the assay procedure provided. Following stimulation, detection reagents were added and signal was detected after 1 hour using the PathHunter® Detection Kit (93-0001). An assay window of 7.6 fold was observed and the EC50 for the ligand insulin was 2.0 ng/ml.

10K cells/well IGF1R-PK SH2-containing protein-EA double stable cells were plated in a 384-well plate, stimulated with IGF1 (Peprotech, Cat #/AF-100-11), a known ligand for IFG1R for 3 hours at room temperature according to the assay procedure provided. Following stimulation, detection reagents were added and signal was detected after 1 hour using the PathHunter® Detection Kit (93-0001). An assay window of 4.4 fold was observed and the $EC_{50}$ for the ligand IGF1 was 17 ng/ml. The results are reported in FIG. 5.

10 k cells/well INSR-PK SH2-containing protein-EA double stable cells were plated in a 384-well plate, stimulated with insulin, a known ligand for INSR, for 3 hours at room temperature according to the assay procedure provided. Following stimulation, detection reagents were added and signal was detected after 1 hour using the PathHunter® Detection Kit (93-0001). An assay window of 7.6 fold was observed and the $EC_{50}$ for the ligand IGF1 was 2.0 ng/ml.

Figure 7:
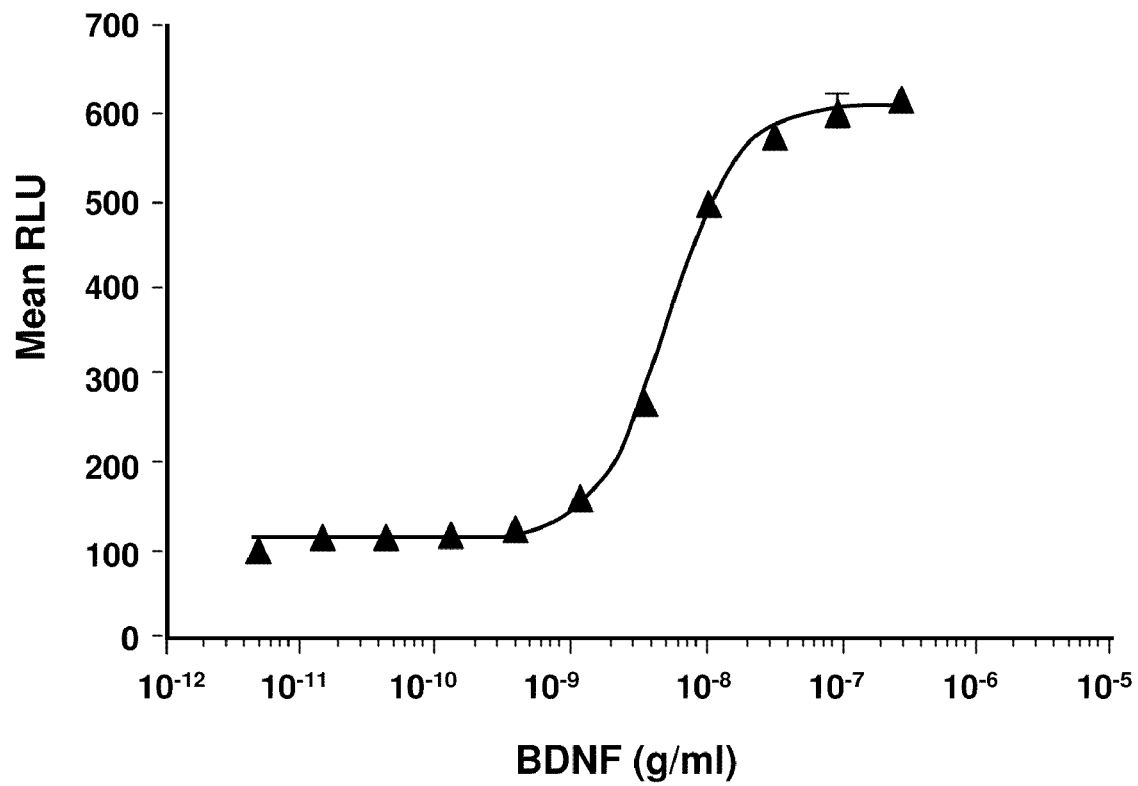
FIG. 7 is a graph of the dose response in U2OS cells of TrkB fused to a low affinity small fragment of β-galactosidase (TrkB-PK). Cells were plated in a 384-well plate at 10,000 cells/well stimulated with BDNF (Peprotech, Cat #/450-02), a known ligand for TrkB, for 3 hours at room temperature according to the assay procedure provided. Following stimulation, detection reagents were added and signal was detected after 1 hour using the PathHunter® Detection Kit (93-0001). An assay window of 4.0 fold was observed and the EC50 for the ligand BDNF was 4.21 ng/ml.

10K cells/well TrkB-PK SH2-containing protein-EA double stable cell were plated in a 384-well plate, stimulated with BDNF (Peprotech, Cat #/450-02), a known ligand for TrkB for 3 hours at room temperature according to the assay procedure provided. Following stimulation, detection reagents were added and signal was detected after 1 hour using the PathHunter® Detection Kit (93-0001). An assay window of 4.0 fold was observed and the $EC_{50}$ for the ligand BDNF was 4.21 ng/ml. The results are reported in FIG. 7.

Figure 8:
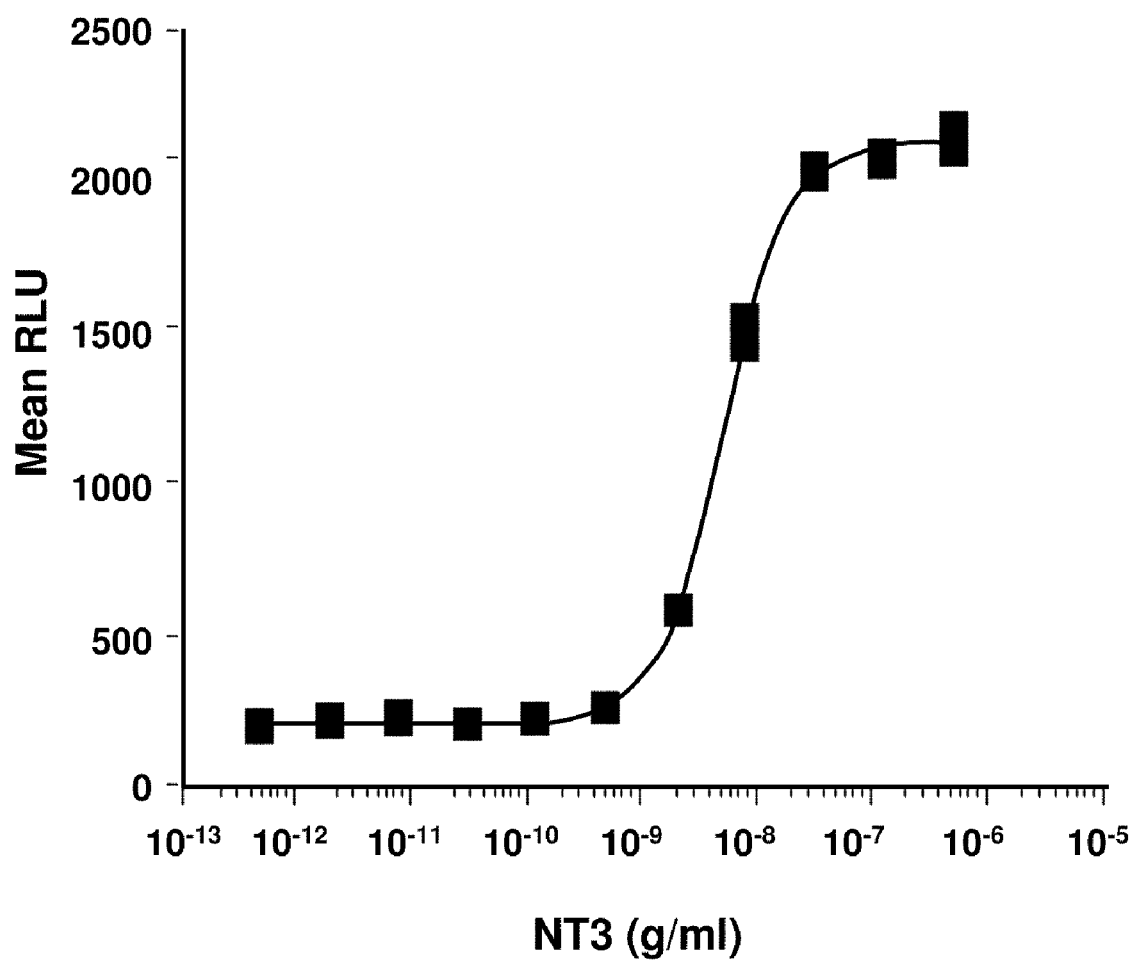
FIG. 8 is a graph of the dose response in U2OS cells of TrkC fused to a low affinity small fragment of β-galactosidase (TrkC-PK). Cells were plated in a 384-well plate at 10,000 cells/well, stimulated with NT3 (Peprotech, Cat #/450-03), a known ligand for TrkC, for 3 hours at room temperature according to the assay procedure provided. Following stimulation, detection reagents were added and signal was detected after 1 hour using the PathHunter® Detection Kit (93-0001). An assay window of 8.1 fold was observed and the EC50 for the ligand NT3 was 7 ng/ml.

10K cells/well TrkC-PK SH2-containing protein-EA double stable cells were plated in a 384-well plate, stimulated with NT3 (Peprotech, Cat #/450-03), a known ligand for TrkC for 3 hours at room temperature according to the assay procedure provided. Following stimulation, detection reagents were added and signal was detected after 1 hour using the PathHunter® Detection Kit (93-0001). An assay window of 8.1 fold was observed and the $EC_{50}$ for the ligand NT3 was 7 ng/ml. The results are reported in FIG. 8.

Figure 9:
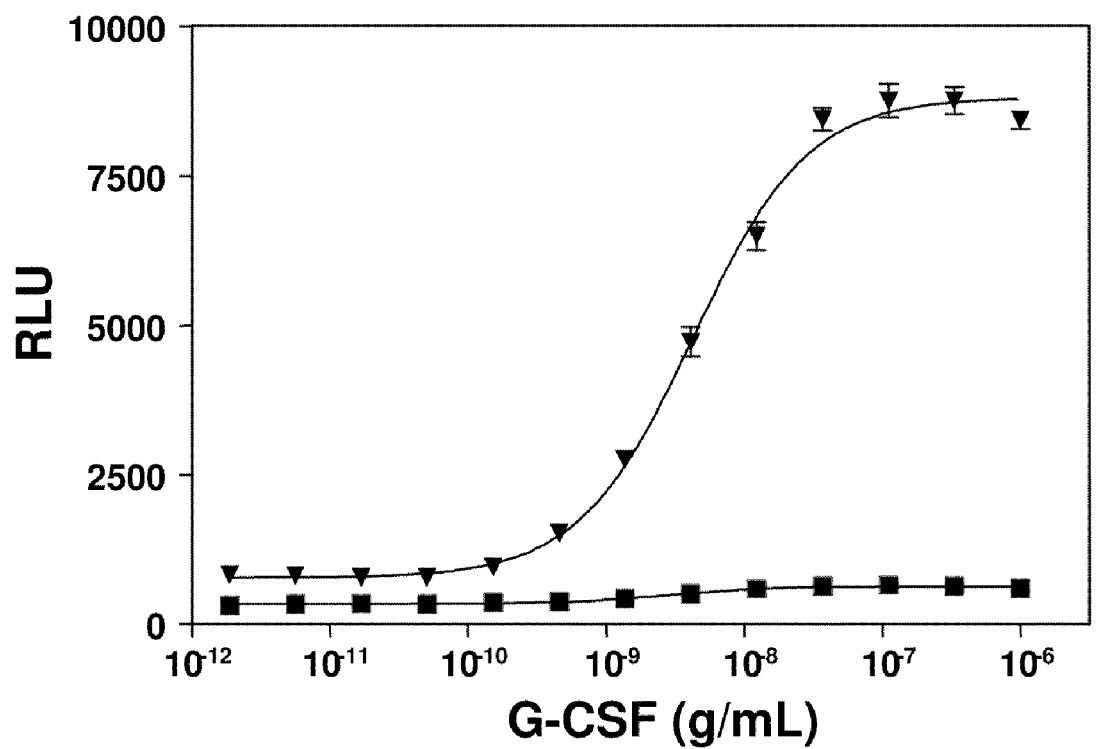
FIG. 9 is a graph of the dose response in U2OS cells of G-CSFR fused to a low affinity small fragment of β-galactosidase (CSF3R-PK). The upper curve is the response in the presence of over expression of Jak2 and the lower curve (squares) is the response in the absence of over expression of Jak2. Cells were plated in a 384-well plate at 10,000 cells/ well, stimulated with G-CSF (Peprotech 300-23), a known ligand for G-CSFR, in PBS+0.1% BSA, for 3 hours at room temperature according to the assay procedure provided. Following stimulation, detection reagents were added and signal was detected after 1 hour using the PathHunter® Detection Kit (93-0001). An assay window of 7 fold was observed and the $EC_{50}$ for the ligand G-CSF was 4 ng/ml.

There are a significant number of TKRs that depend upon cytosolic tyrosine kinases for phosphorylation. The assays for activation of such TKR receptors are substantially the same as described above, except that the cells are triply stable having an expression construct over expressing the cytosolic tyrosine kinase. In the following example, U2OS cells containing the following constructs were used: G-CSFR (granulocyte-colony stimulating factor receptor)-PK with neo selection; SHC1-EA with hygro selection and Jak2 with puromycin selection. The results are reported in FIG. 9.

The genes for the RTK, SH2 and NRTK domains may be obtained from any convenient source; commercial supplier, RT PCR from RNA isolated in accordance with conventional procedures using known sequences as probes, and PCR from genomic DNA using primers from known sequences. The genes are PCR amplified to remove the stop codon at the 3' end and then digested with restriction enzymes where the restriction site is included with the primer sequences. These products are then purified in conventional ways and then ligated into a commercial vector into which the PK or EA has been inserted, in reading frame with the PK or EA. Separating the PK and the EA from the gene is a gly-ser linker that provides flexibility to the fusion proteins to enhance complementation. This linker is not required for activity. The transcriptional regulatory region is generally present in commercial vectors, such as the 5'LTR of the virus used for the vector. Alternatively, the CMV promoter may be used. The resulting vector is then introduced into the host cell by liposome mediated transfection or retrival infection with Moloney murine leukemia virus vector and packaging cell lines. The resulting virus is then used for viral infection. The vectors also include selection genes, such as hygromycin, puromycin and neomycin resistance and cells into which the construct is integrated are selected in a conventional selection medium. The surviving cells are then screened in an agonist dose response assay using the PathHunter® Detection Kit reagents in white-walled microplates.

It is evident from the above results that the subject method provides for a robust accurate assay for measuring agonists and antagonists for RTKs. Cells are provided that can be used effectively in high throughput screening in a cellular environment, so as to closely define the effect of candidate compounds in a mammalian environment. The protocols are easy, use standard equipment and can be readily automated.

CONCLUSION

Although the invention has been described with reference to the above examples, it will be understood that modifications and variations are encompassed within the spirit and scope of the invention. Accordingly, the invention is limited only by the following claims. All references referred to in the specification are incorporated by reference as if fully set forth therein.

What is claimed is:

1. A method for determining phosphorylation of a receptor tyrosine kinase ("RTK"), said method comprising:
   (a) employing a cell comprising
      (i) a first expression construct expressing a fusion of an RTK fused at its C-terminus to a first enzyme fragment, and
      (ii) a second expression construct expressing a fusion of a phosphotyrosine binding peptide fused to a second enzyme fragment, wherein
      said first and second enzyme fragments are fragments of β-galactosidase that have low affinity for each other but when brought together by the binding of said RTK to said phosphotyrosine binding peptide form an active β-galactosidase,
   (b) with the proviso that when said RTK does not autophosphorylate, in the absence of an endogenous active cytosolic tyrosine kinase, a third expression construct is included expressing a cytosolic tyrosine kinase to phosphorylate said RTK;
   (c) incubating said cell for sufficient time (i) for any phosphorylation of said fusion of an RTK fused at its C terminus to a first enzyme fragment to occur to form a phosphorylated RTK and (ii) for any binding to said phosphorylated RTK by said phosphotyrosine binding peptide fused to a second enzyme fragment to occur;
   (d) adding a β-galactosidase substrate to said cell, wherein said substrate forms a detectable product; and
   (e) detecting said detectable product as indicative of the phosphorylation of said RTK.

2. A method according to claim 1, wherein said first fragment is the small fragment of β-galactosidase having fewer than 50 amino acids.

3. A method according to claim 2, wherein said small fragment is mutated.

4. A method according to claim 1, wherein said cell is a mammalian cell.

5. A method according to claim 1, including the additional step of lysing said cell before said detecting.

6. The method of claim 1 wherein said incubating said cell comprises incubating a cell containing a cytosolic tyrosine kinase fused to a first β-galactosidase enzyme fragment.

7. The method of claim 6 wherein said cytosolic tyrosine kinase is a JAK kinase.

8. The method of claim 1 wherein said RTK autophosphorylates upon activation.

9. The method of claim 1 wherein said phosphotyrosine binding peptide is an SH2 domain-containing cytoplasmic protein.

* * * * *